United States Patent [19]

Tung

[11] Patent Number: 5,569,794
[45] Date of Patent: Oct. 29, 1996

[54] VAPOR PHASE PROCESS FOR PRODUCING HYDROFLOUROCARBONS FROM PERCHLOROETHYLENE HAVING A PHENOLIC INHIBITOR

[75] Inventor: Hsueh S. Tung, Getzville, N.Y.

[73] Assignee: AlliedSignal Inc., Morris County, N.J.

[21] Appl. No.: 521,258

[22] Filed: Aug. 30, 1995

Related U.S. Application Data

[63] Continuation of Ser. No. 248,127, May 24, 1994, abandoned.

[51] Int. Cl.$^6$ .................... C07C 17/08; C07C 17/42
[52] U.S. Cl. ............... 570/168; 570/119; 570/166; 570/169
[58] Field of Search ................... 570/119, 166, 570/169, 168

[56] References Cited

U.S. PATENT DOCUMENTS

| | | | |
|---|---|---|---|
| 3,258,500 | 6/1966 | Swamer et al. | 260/653.7 |
| 3,755,477 | 8/1973 | Firth et al. | 260/653.4 |
| 4,034,051 | 7/1977 | Dempf et al. | 570/119 |
| 4,766,260 | 8/1988 | Manzer et al. | 570/168 |
| 4,843,181 | 6/1989 | Gumprecht et al. | 570/169 |
| 4,967,023 | 10/1990 | Carmello et al. | 570/166 |
| 5,091,601 | 2/1992 | Carmello et al. | 570/166 |
| 5,155,082 | 10/1992 | Tung et al. | 502/228 |

*Primary Examiner*—Alan Siegel
*Attorney, Agent, or Firm*—Lois A. Gianneschi

[57] ABSTRACT

An improved process for producing hydrofluorocarbons and hydrochlorofluorocarbons by reacting anhydrous hydrogen fluoride in the vapor phase and in the presence of a fluorination catalyst with an admixture of perchloroethylene and a phenolic inhibitor. The phenolic component is effective to inhibit the formation of an oxidation product in the perchloroethylene while not substantially degrading the fluorination catalyst during the fluorination process. In another embodiment, substantially all of any oxidation inhibitor is removed from the perchloroethylene in-line prior to reacting the hydrogen fluoride with the perchloroethylene.

12 Claims, 1 Drawing Sheet

VAPOR PHASE PROCESS FOR PRODUCING HYDROFLOUROCARBONS FROM PERCHLOROETHYLENE HAVING A PHENOLIC INHIBITOR

This application is a continuation of application Ser. No. 08/248,127, filed May 24, 1994, now abandoned.

FIELD OF THE INVENTION

The invention pertains to an improved process for producing hydrofluorocarbons and hydrochlorofluorocarbons. More particularly, the invention pertains to a vapor phase catalytic process for producing $CF_3CHCl_2$ (HCFC-123), $CF_2ClCHClF$ (HCFC-123a), $CHClFCF_3$ (HCFC-124), $CHF_2CClF_2$ (HCFC-124a), and $CHF_2CF_3$ (HFC-125) from perchloroethylene using a phenolic inhibitor to improve catalyst stability.

BACKGROUND OF THE INVENTION

Hydrofluorocarbons and hydrochlorofluorocarbons are known in the art to be useful in a variety of industrial applications including blowing agents, refrigerants, sterilant gases and solvent applications. While chlorofluorocarbons (CFCs) are known for similar applications, they are believed to be deleterious to the earth's protective ozone layer and it has been desired to develop substitutes which are essentially not ozone depleting. Several such replacement materials have been developed. These include 1,1-dichloro-2,2,2-trifluoroethane (HCFC-123); 1,2-dichloro-1,2,2-trifluoroethane (HCFC-123a); 1-chloro-1,2,2,2-tetrafluoroethane (HCFC-124), 1-chloro-1,1,2,2,-tetrafluorochloroethane (HCFC-124a) and pentafluoroethane (HFC-125). It is expected that the demand for these latter materials will increase dramatically in the future and hence commercially viable processes for their preparation are desired. Many processes for the production of HCFC's and HFC's are known in the art. Typically these processes involve a fluorination using catalysts which have a very short life span and hence they are impractical for commercial application.

U.S. Pat. No. 3,258,500 describes a process for fluorination of halogenated alkanes and alkenes using a gel-type activated chrome oxide catalyst. HCFC-124 and HFC-125 are produced by reacting tetrachloroethylene with anhydrous hydrogen fluoride in the presence of an anhydrous chromium oxide on alumina fluorination catalyst. Catalyst life or stability is not discussed but the process has a low selectivity and yield. U.S. Pat. No. 4,843,181 describes a gas phase process which reacts tetrachloroethylene with hydrogen fluoride in the presence of chromium oxide made from a pyrolysis of $(NH_4)_2Cr_2O_7$. Catalyst stability is not mentioned. This method is disadvantageous since an extremely long contact time is required between the catalyst and the reactants. U.S. Pat. No. 4,967,023 discloses a process which hydrofluorinates perchloroethylene (PCE) with a chromia on $AlF_3$ catalyst. A low conversion of reactants is reported. U.S. Pat. No. 3,755,477 describes an improved chrome oxide catalyst for fluorination of PCE at 360° C. but no catalyst life or stability are reported. Similar processes and low yields are described in U.S. Pat. No. 4,766,260. The gas phase conversion of perchloroethylene to other HCFC's is shown in U.S. Pat. No. 5,091,601. U.S. Pat. No. 5,155,082 describes a partially fluorinated aluminum/chromium oxide catalyst for the hydrofluorination of a halogenated aliphatic hydrocarbon to produce a chlorofluorocarbon, hydrochlorofluorocarbon or hydrofluorocarbon. According to this patent, when HCFC-124 is the desired hydrofluorocarbon the preferred starting material is HCFC-123 or HCFC-123a. HCFC-123 or HCFC-123a, preferably is produced from perchloroethylene as the starting material. None of these references suggest the use of a phenolic type inhibitor in the perchloroethylene.

Heretofore it has been a problem in the art to conduct a vapor phase fluorination of perchloroethylene with anhydrous hydrogen fluoride in the presence of a fluorination catalyst since the perchloroethylene tends to form an oxidation product during storage and transportation. This oxidation product is acidic in nature and forms within the perchloroethylene from atmospheric oxygen and hydrogen from atmospheric moisture. Apparently the perchloroethylene itself tends to break down and form a tarry or carbonaceous material. One proposed solution has been to transport and store the perchloroethylene under a nitrogen blanket. However, this makes handling impractical. Another solution has been to incorporate an amine oxidation inhibitor such as 4-methyl morpholine or diallyl amine in the perchloroethylene. However, such amines cause the fluorination catalyst to have a markedly reduced effectiveness after a relatively short time. Thereafter the fluorination process must be stopped and the catalyst either replaced or reactivated. Typical regeneration requires heating the catalyst to 350° C. for about 12–24 hours. This causes a undesirable loss of production time. The process of this invention also concerns contacting a vapor mixture of perchloroethylene with anhydrous hydrogen fluoride in the presence of a fluorination catalyst. However, it has now been found that by the substitution of a small amount of a phenolic type inhibitor in the perchloroethylene that improved catalyst stability is noticed. In another embodiment of the invention, the inhibitor component is essentially completely removed prior to feeding the purged perchloroethylene to the fluorination reactor. Thus, the process has a more stable operation since the catalyst stability is improved and regeneration cycles are minimized. In practical terms, instead of having to regenerate the catalyst after one or two weeks of service, now several months of service can be expected before a regeneration is necessary. All inhibitors are believed to coke the catalyst, however, the phenolics have been found to do so to a much lesser extent. The result is a more economical process for producing hydrofluorocarbons and hydrochlorofluorocarbons, especially HCFC-123, HCFC-123a, HCFC-124, HCFC-124a, and HFC-125.

SUMMARY OF THE INVENTION

In one embodiment, the invention provides a process for producing hydrofluorocarbons and hydrochlorofluorocarbons by reacting anhydrous hydrogen fluoride in the vapor phase and in the presence of a fluorination catalyst with an admixture of perchloroethylene and an amount of a phenolic oxidation inhibitor component. The amount of inhibitor is that which is effective to inhibit or substantially prevent the formation of oxidation products in the perchloroethylene while not substantially degrading the fluorination catalyst during the fluorination process. In another embodiment, an improved vapor phase catalytic fluorination is done by an in-line removal of substantially all of any oxidation inhibitor from the perchloroethylene prior to reacting it with the hydrogen fluoride.

DETAILED DESCRIPTION OF THE INVENTION

Figure 1:
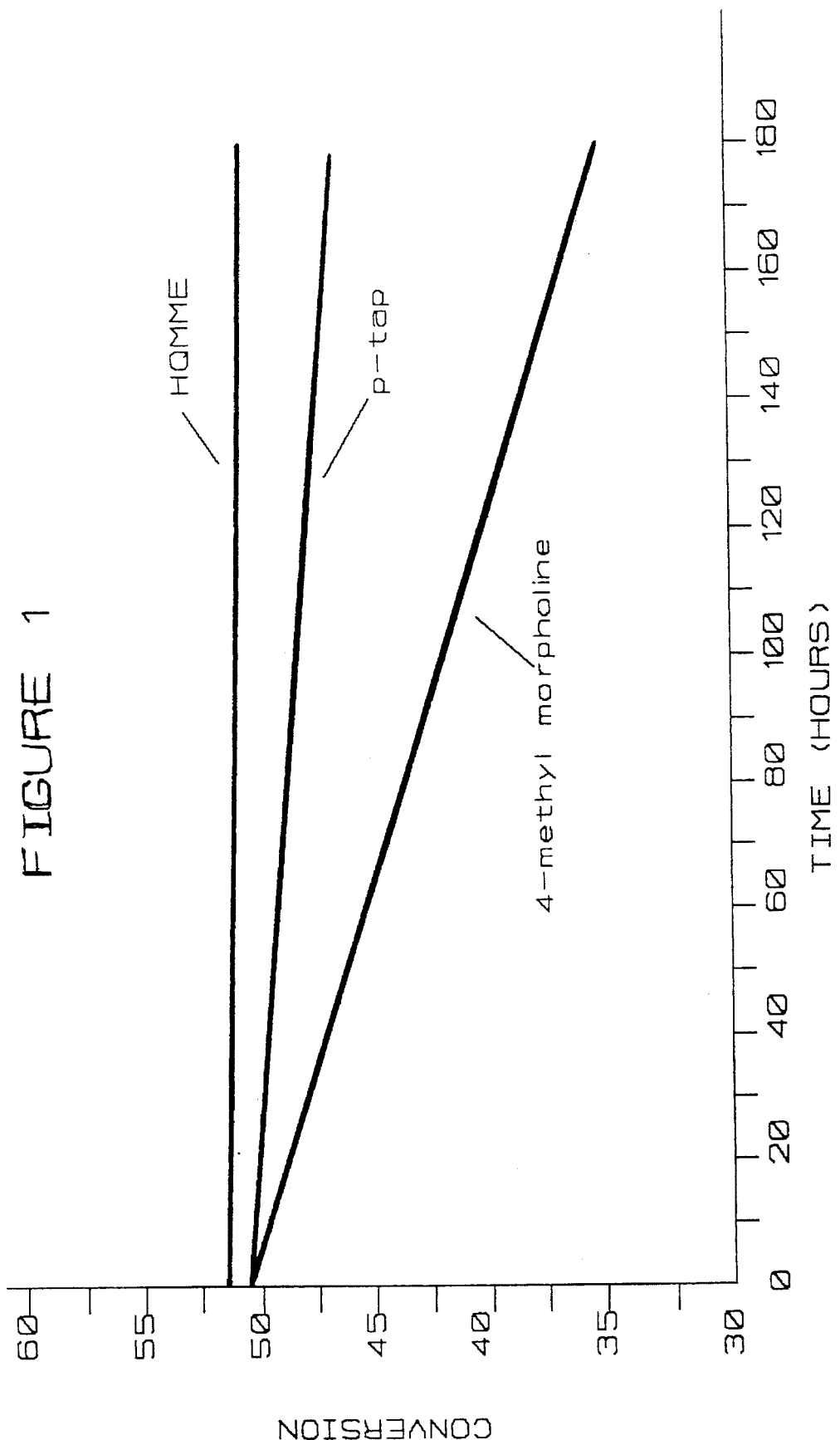
FIG. 1 shows a schematic representation of an inhibitor evaluation.

The first step in the production of hydrofluorocarbons and hydrochlorofluorocarbons is to provide inflowing streams of hydrogen fluoride and perchloroethylene. In one embodiment of the invention the perchloroethylene is provided in admixture with a phenolic oxidation inhibitor. Preferred phenolic oxidation inhibitors non-exclusively include para-tertiary-amyl phenol (p-tap), and quinones such as hydroquinone monomethyl ether (HQMME) and hydroquinone. The amount of inhibitor in the perchloroethylene is that amount which is effective to inhibit or prevent the formation of an oxidation product in the perchloroethylene during storage and transportation and yet not substantially degrade the fluorination catalyst during the subsequent fluorination process. Such an amount preferably ranges from about 1 to about 50 ppm, more preferably from about 1 to about 20 ppm and most preferably from about 1 to about 10 ppm based on the weight of perchloroethylene.

In another embodiment of the invention, the perchloroethylene is in-line removed of inhibitor prior to the subsequent fluorination process. This is effective both for phenolic and non-phenolic inhibitor types. This removal can be done, for example by causing the mixture of perchloroethylene and inhibitor to pass through a molecular sieve desicant or a bed of solid particulate caustic, e.g. in the form of pellets or flakes. Sodium hydroxide or potassium hydroxide are most preferred for this purpose. The caustic causes the inhibitor to be removed in the form of solid particles.

Either the perchloroethylene with the phenolic inhibitor or perchloroethylene which has been purged of inhibitor is then reacted with anhydrous hydrogen fluoride in the vapor phase in the presence of a fluorination catalyst. Usually, the gaseous mixture will be passed through a bed of the catalyst in a reaction tube. While the reaction may be conducted in any suitable reaction vessel, it should be constructed from materials which are resistant to the corrosive effects of hydrogen fluoride at temperatures up to 700° C. for extended periods of time. Suitable materials for construction of the reaction tube include Hastelloy C nickel alloy, Inconel nickel alloy, nickel, and platinum. The most preferred materials are HASTALLOY, INCONEL and MONEL.

The mole ratio of hydrogen fluoride to perchloroethylene is adjusted to be from about 2:1 to about 50:1, and preferably from about 5:1 to about 40:1, and most preferably from about 6:1 to about 20:1. The temperature at which the reaction is conducted preferably ranges from about 200° C. to about 600° C., or more preferably from about 250° C. to about 500° C. and most preferably from about 300° C. to about 400° C. in the reactor. The reactor is preferably a fixed bed reactor filled with a fluorination catalyst. The organic vapor is allowed to contact the fluorination catalyst for from about 0.5 to about 120 seconds, more preferably from about 2 to about 90 seconds and most preferably from about 10 to about 60 seconds. For purposes of this invention, contact time is the time required for the gaseous reactants to pass through the catalyst bed assuming that the catalyst bed is 100% void. The reactive pressure preferably ranges from about atmospheric pressure to about 400 psig, preferably from about 50 to about 300 psig and most preferably from about 100 to about 250 psig. Any of the fluorination catalysts known in the art may be used. Such fluorination catalysts non-exclusively include chromium, aluminum, cobalt, manganese, nickel and iron oxides, halides, oxyhalides and inorganic salts, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$ and $NiCl_2/AlF_3$. Chromium oxide/aluminum oxide catalysts are described in U.S. Pat. No. 5,155,082 which is incorporated herein by reference. The chromium oxide may be crystalline chromium oxide or amorphous chromium oxide. Amorphous chromium oxide is preferred. Chromium oxide ($Cr_2O_3$) is a commercially available material which may be purchased in a variety of particle sizes. Chromium oxide may be purchased, for example, from Great Western Inorganics of Golden, Colo. and Mallinckrodt Specialty Chemicals Company, St. Louis Mo. In the preferred embodiment, a small amount of gaseous oxygen or air flows through the chromium oxide to maintain catalyst activity. The amount of air or oxygen supplied to the reactor is preferably from about 0.01 to about 30 mole percent of oxygen relative to the total organics fed to the reactor. A more preferred amount ranges from about 0.05 to about 20 mole percent and most preferably from about 0.1 to about 10 mole percent. The resulting product mixture includes HCFC-123, HCFC-123a, HCFC-124, HCFC-124a, and HCFC-125. It will be readily appreciated that the respective amounts of the components of the product mixture will vary depending upon reaction conditions and catalysts employed. The product mixture may then be subjected to any subsequent steps desired such as distillation, phase separation, scrubbing, component separation and recycling back to the vapor reactor. These processes are well known to the skilled artisan and are described in the art. The process of the invention provides the above mentioned hydrofluorocarbons and hydrochlorofluorocarbons as the major product at high productivity, normally greater than 10 lbs/hr/ft$^3$. As used herein, the term "major product" means the product that is produced by the reactive system in the greatest amount, usually in an amount of at least 50% by weight.

The following non-limiting examples serve to illustrate the invention.

EXAMPLE 1

Approximately 100 ml chrome oxide catalyst ($Cr_2O_3$) was charged into a 1" monel pipe reactor. This catalyst was dried using nitrogen gas (350 cc/min) at 350° C. for 8 hours. Subsequently, it was treated with anhydrous HF (1 ml/min) at 350° C. for an additional 8 hours. Then, the temperature was lowered to 300° C. and the pressure was raised to 200 psig. Perchloroethylene which contains 10 ppm of HQMME stabilizer was fed into the reactor at a rate of approximately 1 g/min. Air was also fed into the reactor at about 2 mole % of $O_2$/PCE. The experiment was run for about 180 hours. The conversion expressed in PCE % consumed is plotted against time as shown in FIG. 1. The slope of the curve which represents the rate of catalyst deactivation is obtained as 0.004% PCE conversion per hour as listed in Table 1.

EXAMPLE 2

The same reactor and catalyst as in Example 1 were used. The catalyst was regenerated with air to ensure its activity. The same reaction conditions described in Example 1 were used except that the perchloroethylene contains 10 ppm of p-tap stabilizer instead of HQMME. The experiment was run for about 180 hours. PCE conversion is plotted in FIG. 1. The catalyst deactivation rate which is the slope of the curve is calculated as 0.02% PCE conversion per hour. This deactivation rate is shown in Table 1 for comparison.

EXAMPLE 3 (COMPARATIVE)

The same reactor and catalyst as in Example 1 was used and the catalyst was regenerated to ensure its activity. The reaction conditions described in Example 1 were used except that the perchloroethylene contains 50 ppm of 4-methyl-morpholine as stabilizer. The experiment was run for about 180 hours. PCE conversion is again plotted against time. The rate of catalyst deactivation is determined using the slope of the curve. It is calculated as 0.083% PCE conversion per hour. This deactivation rate is shown in Table 1 for comparison.

As indicated in Table 1, the non-phenol type stabilizer such as 4-methylmorpholine deactivates the catalyst rapidly. The regeneration cycle is calculated based on conversion changes from 60% to 30% for each cycle. It can also be seen from Table 1 that the fluorination process using PCE containing 10 ppm HQMME gives the longest regeneration cycle, 7500 hours continuous operation. The process using 4-methyl-morpholine as stabilizer has to shut down every 361 hours to regenerate the catalyst. Frequent interruption makes this process less economical.

TABLE 1

| STABILIZER | DEACTIVATION RATE | REGENERATION CYCLE |
| --- | --- | --- |
| 4-methyl morpholine (50 ppm) | 0.083% conversion/hr. | 361 hours |
| p-t-amyl phenol (10 ppm) | 0.02% conversion/hr. | 1,500 hours |
| HQMME (10 ppm) | 0.004% conversion/hr. | 7,500 hours |

EXAMPLE 4

Commercially obtained perchloroethylene containing 4-methyl morpholine is allowed to flow into a bed of particulate molecular sieve. The outflow product is substantially pure perchloroethylene. The substantially pure perchloroethylene is fed into a 1 inch reactor made from MONEL at a rate of 60 g/hr. The reactor contains 110 ml of an amorphous $Cr_2O_3$ catalyst. The reactor temperature is 330° C. and the pressure is 50 psig. Anhydrous hydrogen fluoride is simultaneously fed to the reactor at the rate of 58.2 g/hr. The mole ratio of HF to PCE is 8. Air is co-fed to the reactor at an $O_2$: PCE mole ratio of about 2 mole %. The catalyst contact time is 11 seconds. The resultant product contains a mixture of HCFC-123, HCFC-123a, HCFC-124, HCFC-124a, and HFC-125 which are then separated into their component parts.

What is claimed is:

1. A process for producing hydrofluorocarbons and hydrochlorofluorocarbons which comprises reacting anhydrous hydrogen fluoride in the vapor phase and in the presence of a fluorination catalyst with an admixture of perchloroethylene and an oxidation inhibitor, wherein the oxidation inhibitor is selected from the group consisting of hydroquinone monomethyl ether and hydroquinone in an amount of from about 1 ppm to about 50 ppm based on the weight of perchloroethylene.

2. The process of claim 1 wherein the hydrofluorocarbons and hydrochlorofluorocarbons produced are a major amount of one or more components selected from the group consisting of $CF_3CHCl_2$, $CF_2ClCHClF$, $CHClFCF_3$, $CHF_2CClF_2$, and $CHF_2CF_3$.

3. The process of claim 1 wherein the oxidation inhibitor is present in admixture with the perchloroethylene in an amount ranging from about 1 ppm to about 10 ppm based on the weight of perchloroethylene.

4. The process of claim 1 wherein the mole ratio of hydrogen fluoride to perchloroethylene ranges from about 2:1 to about 50:1.

5. The process of claim 1 wherein the reaction is conducted at a temperature which ranges from about 200° C. to about 600° C.

6. The process of claim 1 wherein the reactants contact the fluorination catalyst for from about 0.5 to about 120 seconds.

7. The process of claim 1 wherein the reaction pressure ranges from about atmospheric pressure to about 400 psig.

8. The process of claim 1 wherein the fluorination catalyst is selected from the group consisting of chromium, aluminum, cobalt, manganese, nickel and iron oxides, halides, oxyhalides and inorganic salts, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$ and $NiCl_2/AlF_3$.

9. The process of claim 1 wherein air or oxygen supplied to the reactor in an amount of from about 0.01 to about 30 mole percent of oxygen based on the amount of the total organics fed to the reactor.

10. The process of claim 1 further comprising conducting one or more subsequent steps to the reaction product selected from the group consisting of distillation, phase separation, scrubbing, component separation and recycling a portion of the reaction product back as reaction feed.

11. The process of claim 1 wherein the oxidation inhibitor is hydroquinone monomethyl ether.

12. The process of claim 1 wherein the oxidation inhibitor is hydroquinone.

* * * * *